United States Patent [19]

Albeck et al.

[11] Patent Number: 5,102,908
[45] Date of Patent: Apr. 7, 1992

[54] METHOD OF TREATING ACQUIRED IMMUNEDEFICIENCY SYNDROME (AIDS) USING ORGANIC TELLURIUM AND SELENIUM DERIVATIVES

[76] Inventors: Michael Albeck, 8 Harel Street, Ramat Gun; Benjamin Sredni, Yona Hanavi St 22, Bnei Brak, both of Israel

[21] Appl. No.: 531,887

[22] Filed: Jun. 1, 1990

Related U.S. Application Data

[60] Division of Ser. No. 107,131, Oct. 9, 1987, Pat. No. 4,962,207, which is a continuation-in-part of Ser. No. 782,129, Sep. 30, 1985, Pat. No. 4,761,480, which is a continuation-in-part of Ser. No. 712,549, Mar. 15, 1985, abandoned, which is a continuation-in-part of Ser. No. 599,511, Apr. 12, 1984, abandoned.

[51] Int. Cl.⁵ .................. A01N 43/26; A01N 43/02; A01N 43/32; A01N 43/12
[52] U.S. Cl. .................... 514/467; 514/450; 514/452; 514/462; 424/85.1
[58] Field of Search .............. 424/85.1; 514/450, 452, 514/462, 467

Primary Examiner—Frederick E. Waddell
Assistant Examiner—Gregory Hook
Attorney, Agent, or Firm—Hedman, Gibson & Costigan

[57] ABSTRACT

A method for the treatment of Acquired Immune Deficiency Syndrome is disclosed, which is based on the administration of a tellurium derivative of the formula:

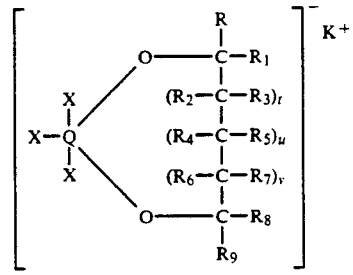

wherein Q is Te or Se; t is 1 or 0; u is 1 or 0; v is 1 or 0; $R$, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbon, cyanoalkyl of 1 to 5 carbons, alkoxy of 1 to 5 carbon atoms, alkoxyalkyl of 2 to 10 carbons atoms and —$COR_{10}$ wherein $R_{10}$ is alkyl of from 1 to 5 carbons; and X is halogen.

2 Claims, No Drawings

METHOD OF TREATING ACQUIRED IMMUNEDEFICIENCY SYNDROME (AIDS) USING ORGANIC TELLURIUM AND SELENIUM DERIVATIVES

This is a divisional application of U.S. patent application Ser. No. 07/107,131, filed Oct. 9, 1987, now U.S. Pat. No. 4,962,207, which is a continuation-in-part of U.S. patent application Ser. No. 06/782,129, filed Sept. 30, 1985; which is U.S. Pat. No. 4,761,480; which is a continuation-in-part of U.S. patent application Ser. No. 06/712,549, filed Mar. 15, 1985, now abandoned; which is a continuation-in-part of U.S. patent application Ser. No. 06/599,511, filed Apr. 12, 1984, now abandoned.

BACKGROUND OF THE INVENTION

It is well known that the growth of normal lymphocytes is dependent not only on contact with an antigenic substance or a mitogen, but also on the presence of certain growth factors known as lymphokines. One of these growth factors is known as T-cell growth factor (TCGF) better known as interleukin-2 (IL-2). The discovery of this growth factor (Gillis, et al., Nature, 268; 154 (1977) and Ruscetti, et al., J. Immunol, 119; 131 (1977)) resulted in the large scale growth and cloning of T-lymphocytes as sources for IL-2.

The lymphocytes or white blood cells in the animal body come in two types, B-cells and T-cells. The B-cells produce antibodies in the form of immunoglobulins that bind onto invading organisms while the T-cells produce the lymphokines which are responsible for turning B-cells on or off. See for example Cell. Immunol. 36:15 (1978); J. Cell Physiol. 96:53 (1978); Eur. J. Immunol. 8:681 (1978); Immunol. Rev. 54:188 (1981); Immunol. Rev. 54:158 (1981); J. Exp. Med. 154:1500 (1981); National Cancer Institute Mon. 60:211 (1982); Int. J. Cancer 28:157 (1981); The Potential Role of T-Cell Subpopulations in Cancer Therapy, Eds. A. Fefer & A. Goldstein, Raven Press, N.Y. pp 173 et seq. (1982); J. Immunol, 128:(258) 1982.

The known types of lymphokines include, in addition to IL-2, B-cell factors, macrophage activation factor (MAF), Interleukin-3 (IL-3), Colony Stimulating Factor (CSF), Tumor Necrosis Factor, and other factors produced by monocytes such as Interleukin-1 (IL-1) and Gamma Interferon. All of these factors are secreted by white blood cells and are collectively known as cytokines. Great attention has been given to using various recombinant DNA techniques and other methodologies for cloning normal T and B cell lines that can produce these materials. See for example Nature 259:130 (1976); Immunology 32:319 (1977); Exp. Hemat, 8:494 (1980); Nature 283:581 (1980); Proc. Natl. Acad. Sci. U.S.A. 78:1858 (1981); J. Immunol. Methods 49:1 (1982); Nature 29424/31 697–699 (1981), all of which are incorporated by reference.

The present invention is based on the discovery of a class of synthetic organic derivatives of tellurium or selenium that are capable of stimulating cytokine producing cells to produce significant quantities of cytokines both in vivo and in vitro. This discovery makes possible a novel therapeutic approach in the treatment of cancer, immune deficiencies, autoimmune diseases and infectious diseases.

Accordingly, it is an object of the invention to provide novel compounds based on tellurium or selenium that are useful as therapeutic agents.

It is also an object of the invention to provide a novel method for producing in vitro cytokines such as lymphokines and induce receptors to these cytokines.

It is also an object of the invention to produce in vivo cytokines such as lymphokines and produce in vivo cytokines such as lymphokines and induce receptors for cytokines for the treatment of diseases such as cancer, immune deficiencies, autoimmune diseases and infectious diseases.

It is also an object of the invention to provide novel pharmaceutical compositions that are based on tellurium compounds that produce cytokines in vivo and in vitro.

SUMMARY OF THE INVENTION

The derivatives of tellurium or selenium that are useful in the present invention includes those compounds of the following general formulas which stimulate cells to produce lymphokines:

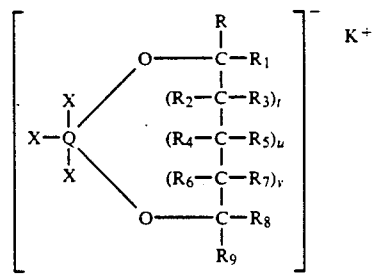

wherein Q is Te or Se; t is 1 or 0; u is 1 or 0; v is 1 or 0; $R, R_1, R_2, R_3, R_4, R_5, R_6, R_7, R_8$ and $R_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and $-COR_{10}$ wherein $R_{10}$ is alkyl of from 1 to 5 carbons; and X is halogen; while the potassium salt is illustrated, it is understood that other pharmaceutically acceptable salts are within the scope of the invention. The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term haloalkyl of 1 to 5 carbon atoms includes chloromethyl; 2-iodoethyl; 4-bromo-nbutyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes $-CH_2CONH_2$; $-CH_2CH_2CONH_2$; $-CH_2CH_2CH_2CONH_2$ and the like; the term cyanoalkyl includes $-CH_2CN$; $-CH_2CH_2CN$; $-CH_2CH_2CH_2CN$ and the like; the term alkoxy of 1 to 5 carbon atoms includes methoxy, ethoxy, n-propoxy, n-pentoxy and the like; the terms halo and halogen are used to signify chloro, bromo, iodo and fluoro; the term acyl includes $R_{16}CO$ wherein $R_{16}$ is H, or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_3)_2$. Compounds which are based on tellurium are the presently preferred compounds of the invention. The tellurium based compounds that are preferred include those of the formula:

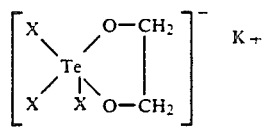

wherein X is halogen. The preferred halogen species is chloro. These compounds are capable of inducing lymphokine production such as IL-2 formation as well as the proliferation of IL-2 producer cells and the activation of IL-2 receptor sites.

Useful dihydroxy compounds for use in the preparation of compounds of structure A or B. include those of formula I wherein R, $R_1$, $R_4$ and $R_5$ are as shown in the Table:

TABLE $$\begin{array}{c} R \quad R_4 \\ | \quad | \\ HO-C-C-OH \\ | \quad | \\ R_1 \quad R_5 \end{array} \quad (I)$$

| R | $R_1$ | $R_4$ | $R_5$ |
|---|---|---|---|
| H | H | H | H |
| H | Cl | H | H |
| H | $OCH_3$ | H | H |
| H | $COOCH_3$ | H | H |
| H | H | CN | H |
| H | CHO | H | H |
| H | H | COOH | H |
| H | $CH_2COOH$ | H | H |
| H | H | $CHCOOCH_3$ | H |
| H | I | H | H |
| H | H | Br | H |
| H | H | $CONH_2$ | H |
| H | H | $CH_2OH$ | H |
| H | COOH | H | H |

Other dihydroxy compounds for use in the preparation of compounds A and B include those of formula II wherein R, $R_1$, $R_2$, $R_3$, $R_4$ and $R_5$ are as shown in the Table:

$$\begin{array}{c} R \quad R_2 \quad R_4 \\ | \quad | \quad | \\ HO-C-C-C-OH \\ | \quad | \quad | \\ R_1 \quad R_3 \quad R_5 \end{array} \quad (II)$$

| R | $R_1$ | $R_2$ | $R_3$ | $R_4$ | $R_5$ |
|---|---|---|---|---|---|
| H | H | H | H | H | H |
| H | H | Cl | H | H | H |
| H | $CH_2OH$ | H | H | H | H |
| H | H | OH | H | H | H |
| H | H | H | $CH_3$ | H | H |
| H | H | H | $CH_2Cl$ | H | H |
| H | H | H | COOH | H | H |
| H | H | H | $CH_2COOH$ | H | H |
| H | H | H | CHO | H | H |
| H | H | H | H | H | $CH_2CHO$ |
| H | H | $CONH_2$ | H | $H_2$ | $CH_3$ |
| H | H | H | CN | H | H |
| H | H | H | H | $CH_2CONH_2$ | H |
| H | H | H | $COOCH_3$ | $H_3$ | H |
| H | $H_3$ | $OCH_3$ | H | H | H |

Other dihydroxy compounds for use in making compound of formula A and B include those of formula III wherein R, $R_1$, $R_2$, $R_3$, $R_4$ and $R_5$ are as shown in the Table.

$$\begin{array}{c} R \quad R_2 \quad R_4 \quad R_8 \\ | \quad | \quad | \quad | \\ HO-C-C-C-C-OH \\ | \quad | \quad | \quad | \\ R_1 \quad R_3 \quad R_5 \quad R_9 \end{array} \quad (III)$$

| R | $R_1$ | $R_2$ | $R_3$ | $R_4$ | $R_5$ | $R_8$ | $R_9$ |
|---|---|---|---|---|---|---|---|
| H | H | H | H | H | H | H | H |
| H | H | Cl | H | H | H | H | H |
| H | H | H | H | Br | H | H | H |
| H | H | $OCH_3$ | H | H | H | H | H |
| H | $H_2$ | $CONH_2$ | H | H | H | H | H |
| H | Br | H | H | Br | H | H | H |
| H | H | H | H | $CH_2COOH$ | H | H | H |
| H | H | Cl | Cl | H | H | H | H |
| H | $CH_2COOH$ | H | H | H | H | H | H |
| H | H | $CH_3$ | H | H | H | H | H |
| H | $CH_3$ | H | H | H | H | H | H |
| H | $CH_2Cl$ | H | H | H | H | H | H |
| H | H | H | I | H | H | H | H |
| H | $CH_2CN$ | H | H | H | H | H | H |
| H | H | H | H | $CH_2CH_2OH$ | H | H | H |

Additional dihydroxy compounds include those of formula IV wherein R, $R_1$, $R_2$, $R_3$, $R_4$ and $R_5$ are as shown in the Table.

$$\begin{array}{c} R \quad R_2 \quad R_4 \quad R_6 \quad R_8 \\ | \quad | \quad | \quad | \quad | \\ HO-C-C-C-C-C-OH \\ | \quad | \quad | \quad | \quad | \\ R_1 \quad R_3 \quad R_5 \quad R_7 \quad R_9 \end{array} \quad (IV)$$

| R | $R_1$ | $R_2$ | $R_3$ | $R_4$ | $R_5$ | $R_6$ | $R_7$ | $R_8$ | $R_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | $CONCH_3$ | H | H | H | Br | H | H | H |
| H | H | Br | H | H | H | $CON(CH_3)_2$ | H | H | H |
| H | H | H | $OCH_3$ | H | H | H | H | H | H |
| H | H | H | H | $OCH_3$ | H | H | H | H | H |
| H | H | H | H | $CH_2COOH$ | H | H | H | H | H |
| H | H | COOH | H | H | H | H | H | H | H |
| H | $CH_3$ | H | H | H | H. | H | H | H | H |

-continued $$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-\underset{\underset{R_7}{|}}{\overset{\overset{R_6}{|}}{C}}-\underset{\underset{R_9}{|}}{\overset{\overset{R_8}{|}}{C}}-OH \qquad (IV)$$

| R | $R_1$ | $R_2$ | $R_3$ | $R_4$ | $R_5$ | $R_6$ | $R_7$ | $R_8$ | $R_9$ |
|---|---|---|---|---|---|---|---|---|---|
| $CH_3$ | H | H | H | H | H | $CH_3$ | H | H | H | H |
| H | $CH_2CH_3$ | H | H | H | H | H | Cl | H | H |
| H | $CH_2CN$ | H | H | $CH_2OH$ | H | H | H | H | H |
| H | H | H | I | H | H | H | H | CN | H |
| H | $CH_2CH_2COOH$ | H | H | H | H | H | H | H | H |
| H | H | CHO | H | H | H | H | H | H | H |
| H | H | H | F | H | H | H | H | H | H |

The compounds are made by combining substantially equimolar amounts of tellurium tetrahalide with a dihydroxy compound in a suitable reactor at room temperature or at elevated temperatures up to the reflux temperature. It is preferred to avoid using any solvent. The preferred method requires heating the reaction mixture to about 60°-90°, preferably 80° while stirring the reaction mixture with a suitable magnetic or mechanical stirrer. The reaction may be carried out for a sufficient period of time to ensure complete reaction of the reactants. This time will vary with the reaction conditions, the particular compound being made. An appropriate salt such as an alkali metal halide or ammonium halide is added to the reaction mixture at the start of the reaction. Suitable salts include potassium chloride and ammonium chloride. The reaction may be run at atmospheric pressure but if desired, it may be carried out at reduced or elevated pressure. The reaction is preferably carried out in the presence of an oxygen containing atmosphere such as air but inert atmospheres such as nitrogen, argon, helium or mixtures thereof may be utilized if desired. Reaction times of 1 minute to 168 hours may be used although reaction times of 6-16 hours are preferred.

The reactor should be of glass construction or lined with glass or other ceramic material that is inert with respect to the reactants.

Usually the compounds produced in the process will precipitate as the reaction mixture is cooled to room temperature. Precipitation may also be effected by adding a suitable precipitant such as a liquid alkane such as hexane or by concentration of the reaction mixture by solvent removal by evaporation with or without the aid of vacuum. The product may be collected in a sintered glass filter, washed with a cold solvent and dried using conventional techniques. The product is stored in a suitable container, protected from light, and preferably at reduced temperature to avoid decomposition.

The solvent system for administration of the compounds of the invention may be based on dimethylsulfoxide or lower alkanols such as ethanol and propanol, glycols such as ethylene glycol, glycerol, propylene glycol and the like. The preferred solvent system is a phosphate buffered saline solution which contains an amount of sodium acid phosphate and sodium phosphate in water to give a pH of 7.1-7.2 (PBS).

Those skilled in the art will appreciate that the presence of a reactive group that will interfere with the synthesis of a particular compound will require the use of a protective group that is removable using known methods.

The compounds of the invention may be administered to mammals for treatment of cancer, immune deficiencies, autoimmune diseases and infectious diseases using amounts that are effective in each condition. The treatment will alleviate the symptoms of these diseases by causing the mammalian body to produce increased amounts of lymphokines. The invention also includes the in vitro production of increased amounts of cytokines such as lymphokines and or their receptors and the use of these materials and/or as therapeutic agents to be administered to mammals for the alleviation of cancer, immune deficiences and infectious diseases. It is contemplated that the composition of the invention may be used in combination with other anti-cancer chemotherapeutic agents such as cyclophosphamide.

The term cancer is used to include leukemia and solid tumors that arise spontaneously, by contact with a carcinogenic agent, by irradiation or by oncoviruses. These conditions are well known to those who are skilled in the art and include such conditions as adrenal tumors, bone tumors, gastrointestinal tumors, brain tumors, breast tumors, skin tumors, lung tumors, ovarian tumors, genitourinary tumors and the like. The Merck Manual 13th Edition, Merck & Co. (1977) describes many of these conditions. Pages 647-650; 828-831; 917-920; 966; 970-974; 1273, 1277; 1371-1376; 1436-1441; 1563; 1612-1615 of the publication are incorporated herein by reference.

The term immunodeficiency diseases is used to describe a diverse group of conditions such as Acquired Immunedeficiency Syndrome (AIDS) characterized chiefly by an increased susceptibility to various infections with consequent severe acute, recurrent and chronic disease which result from one or more defects in the specific or nonspecific immune systems. Pages 205-220 of the Merck Manual 13th Edition describe many of these conditions and they are incorporated herein by reference.

The term autoimmune diseases includes disorders in which the immune system produces autoantibodies to an endogenous antigen, with consequent injury to tissues. Pages 241-243 of the Merck Manual 13th Edition describe these conditions and they are incorporated herein by reference.

The term infectious diseases includes those pathologic conditions that arise from bacterial, viral or fungus organisms that invade and disrupt the normal function of the mammalian body. Pages 3-149 of the Merck Manual 13th Edition describe these conditions and they are incorporated herein by reference.

The compounds may be administered orally, parenterally, transcutaneously, topically or by contacting mucous membranes. The compounds may be administered orally in capsules or tablets that may be prepared using conventional excipients, binders, disintegrating agents and the like. The parenteral route is presently preferred and compositions may be prepared by dissolving the compound in a suitable solvent such as an aqueous buffer and dimethyl sulfoxide or glycerol. The parenteral route may be intramuscular, intravenous, intradermal using a sustained release carrier or subcutaneous. The concentration of the compounds in combination with a pharmaceutical carrier is not critical and is a matter of choice. Remingtons Practice of Pharmacy, 9th, 10th and 11th Ed. describe various pharmaceutical carriers and is incorporated herein by reference.

It has been found that a number of the tellurium compounds useful in the practice of the invention will hydrolyze in the presence of water. These hydrolyzed compositions are active in vivo and in vitro although the hydrolyzed compositions eventually decompose and lose their ability to induce lymphokine secretion. For this reason, the compositions should be freshly prepared. If the compounds are administered orally in dry form, they are active in inducing the production of lymphokines. Preferably, the compounds should be kept under anhydrous conditions until just prior to being used.

It has been found that certain compounds such as $TeO_2$ alone will induce lymphokine production in producer T-cell lymphocytes in vitro and in vivo but it will not cause proliferation of lymphokines in producing cells such as IL-2 producer cells or activate the receptor site in responder T-cell lymphocytes. Thus the invention also contemplates the use alone of $TeO_2$ and tellurium compounds that are active as lymphokine inducers.

Topical compositions may be prepared by dispersing the compounds in a hydrophillic or hydrophobic cosmetic base. Petroleum jelly or commercial preparations such as Oil of Olay may be used. The concentration may be from 0.0001-5% on a weight/weight basis.

The dosage of the compounds of the invention used to stimulate lymphokine production or treat the specific disease condition described herein may be varied depending on the particular disease and the stage of the disease. Generally an amount of the compound may be administered which will range from $0.05 \times 10^{-3}$ to $1 \times 10^{-3}$ g/Kg of body weight and preferably from $0.1 \times 10^{-3}$ to $0.5 \times 10^{-3}$ g/Kg of body weight. For example a dosage of 1-3 mg per day for a 75 Kg mammal is contemplated as a sufficient amount to induce lymphokine production but the dosage may be adjusted according to the individual response and the particular condition that is being treated. For the treatment of AIDS 1.0-9.0 mg/m$^2$ may be given IV three times a week. In addition, the compound of the invention may be administered concomitantly with agents such as 9-(1,3-dihydroxy-2-propoxymethyl) guanine (DHPG); and/or AZT.

In addition to treating the mammalian disorders described hereinabove, the compounds may be utilized for veterinary purposes in the treatment of viral and immune diseases that afflict horses, ungulates and fowl. These disorders may be treated using quantities of the compound that may be used in treating the mammalian disorders described hereinabove.

For in vitro use, cells may be stimulated to produce lymphokines by use of $1 \times 10^{-8}$ to $1 \times 10^{-4}$, preferably $1 \times 10^{-7}$ to $1 \times 10^{-5}$ g of compound per $10^6$ cells/ml.

Preliminary toxicity studies in mice have established an $LD_{50}$ of 300 ug./25 g of body weight in 6 week old mice for the compound of Example 1. The compounds may be used as anti-bacterial or anti-viral agents in plants or in animals. Virus infections such as West Nile virus infections in mice are susceptible to the compound of the Example 1 at a dose of 10 μg/day/mouse. Plant bacterial infections such as crown gall caused by *Agrobacterium tumefaciens* may be treated or prevented by the application of a 0.1% solution of compounds of the invention.

The invention also contemplates a method for dissolving the compounds of the invention in an aqueous vehicle. This method comprises the use of ultrasound or mechanical agitation for an extended period of time which will dissolve the compound. Generally ultrasound is produced by a transformer which transforms 50/60 hertz, line voltage AC into high frequency electrical energy which is coupled to a transducer. By using piezoelectric ceramics, electrical frequency is converted into mechanical vibration. Typical amplitudes of 0.0003 for 40 k Hz equipment and 0.00007 to 0.001 for 20 k Hz equipment are useful. The transducer may be provided with a booster that is connected to a horn that has means for conducting the ultrasound to a container that holds the liquid for dissolving the compounds of the invention. Useful devices include small scale ultrasonic cleaners such as the Bronson instrument. It has been found that solutions containing about 5 mg/100 ml of the compound of the invention may be prepared by applying ultrasound for a sufficient period of time to provide an aqueous liquid containing the compound. The time required for this is usually 3 hours to 24 hours. High speed mechanical shakers such as a Tutenhauer shaker or waring blenders may be used for this purpose. The use of an electically operated agitator will cause the compounds to form a solution or dispersion after about 3 to 4 hours of agitation.

It has been discovered that glycerol may be used in the preparation of aqueous liquids that contain the compound. These preparations are then diluted with an aqueous injectable diluent such as water, saline solution etc. The preferred diluent is PBS.

The text of Ser. No. 599,511, filed Apr. 12, 1984 is incorporated herein by references.

DESCRIPTION OF THE PREFERRED EMBODIMENTS

The following examples are given to illustrate the invention and it is understood that they do not limit the scope of the invention.

EXAMPLE 1

0.01 mol of tellurium tetrachloride and 0.01 mol of potassium chloride were added to 10ml of ethylene glycol. The solution was heated at 80° C. and stirred for 4 hours and then cooled to room temperature. A white precipitate is formed immediately. The precipitate is filtered and washed with a minimum of dry acetonitrile. The precipitate is collected and dried in a vacuum for 5 hours. The yield is about 50% of theoretical.

Analysis: Calc: 7.21, 1.20, 31.83, 38.43, 11.71. Found: 7.23, 1.16, 31.76, 38.45, 11.60.

nmr (DMSO-d$_6$) (ppm): 4.4(S).

The product has the structure:

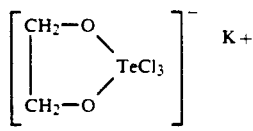

The product was tested and was found to stimulate the production of lympokines.

EXAMPLE 2

0.01 mol of tellurium tetrachloride and 0.01 mol of ammonium chloride were added to 10 ml ethylene glycol. The solution was heated at 80° C. and stirred for 4 hours and then cooled to room temperature. After 8 hours at room temperature, a white precipitate is formed. The precipitate is filtered and washed with a small amount of acetonitril. The precipitate is collected and dried in vacuum for 5 hours. The yield is about 55% of theoretical.

Analysis: Calc: 7.66, 2.55, 4.47, 10.22, 34.02, 42.53. Found: 7.87, 2.42, 4.54, 10.25, 34.26, 40.75.

nmr (DMSO-d6) (ppm) 4.4(S), 7.2 (+).

The product has the structure:

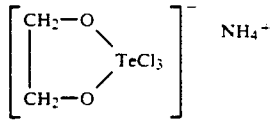

EXAMPLE 3

IL-2 production from mouse spleen cells using the compound of Example 1 was compared with IL-2 product as induced by the ammonium salt analog of the compound of Example 1 in mouse spleen cells at a concentration of $10^7$ cells/ml Enriched RPMI containing 10% fetal calf serum were incubated for 24 hours with varying concentrations of the compounds in the presence of PMA (25 ng/m/cells). Supernatants were collected and tested for IL-2 acitivity using the IL-2 addicted cell-line CTLD.

| Concentration (μg/ml) | Supernatant (cpm) 50% | 25% |
|---|---|---|
| | Example 1 | |
| 5 | 1,987 | 2,608 |

| Concentration (μg/ml) | Supernatant (cpm) 50% | 25% |
|---|---|---|
| | -continued | |
| 1 | 19,207 | 33,928 |
| 0.5 | 56,252 | 99,247 |
| 0.1 | 14,598 | 1,480 |
| | NH4+ Salt Analog Of Example 1 | |
| 5 | 623 | 2,902 |
| 1 | 17,948 | 24,912 |
| 0.5 | 36,515 | 51,567 |
| 0.1 | 31,573 | 28,877 |

We claim:

1. A method for the treatment of acquired immune deficiency syndrome in a patient which comprises administering thereto an effective amount of a compound of the formula:

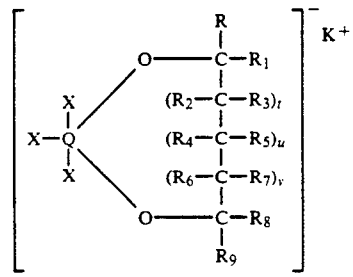

wherein Q is Te or Se; t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbons atoms and $—COR_{10}$ wherein $R_{10}$ is alkyl of from 1 to 5 carbons; and X is halogen.

2. A method as defined in claim 1, wherein the compound:

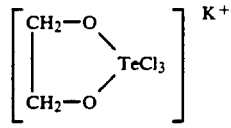

1.0–9.0 mg/m² is administered IV three times a week.

* * * * *